United States Patent [19]

Inoue

[11] Patent Number: 5,006,986
[45] Date of Patent: Apr. 9, 1991

[54] METHOD OF DEMARCATING TWO-DIMENSIONAL DISTRIBUTION

[75] Inventor: Takanobu Inoue, Hyogo, Japan

[73] Assignee: Toa Medical Electronics Co., Ltd., Kobe, Japan

[21] Appl. No.: 279,955

[22] Filed: Dec. 5, 1988

[30] Foreign Application Priority Data

Jun. 7, 1988 [JP] Japan .................................. 63-140309

[51] Int. Cl.$^5$ ........................ G06F 15/42; G01N 21/64
[52] U.S. Cl. .................................. 364/413.08; 356/39
[58] Field of Search .............. 364/555, 413.07, 413.08; 424/3; 356/39; 377/6; 382/6

[56] References Cited

U.S. PATENT DOCUMENTS

| | | | |
|---|---|---|---|
| 3,684,377 | 8/1972 | Adams et al. .......................... | 356/36 |
| 4,082,457 | 4/1978 | Kohno et al. .......................... | 356/39 |
| 4,284,412 | 8/1981 | Hansen et al. ........................ | 436/808 |
| 4,325,706 | 4/1982 | Gersham et al. ...................... | 436/63 |
| 4,661,913 | 4/1987 | Wu et al. .............................. | 364/500 |

Primary Examiner—Jerry Smith
Assistant Examiner—David Huntly
Attorney, Agent, or Firm—Fitch, Even, Tabin & Flannery

[57] ABSTRACT

One particle group in a sample undergoing measurement is demarcated from another particle group in the sample by drawing a discriminant on a plot of a two-dimensional distribution of the particles. To draw the discriminant, the two-dimensional distribution is divided into a grid pattern of a plurality of areas arranged in a number of columns, the number of particles contained in each area is determined, and an area containing the smallest number of particles is selected from a plurality of areas in a specific column. Next, in a column neighboring the specific column, an area containing the smallest number of particles is selected from those areas adjacent the area selected in the specific column. This operation for the neighboring column is thenceforth successively repeated for all subsequent columns to select the area containing the smallest number of particles in each column. Finally, a representative point is set in each area selected in each column, and an approximation curve is obtained by connecting each of the points. The approximation curve serves as the discriminant.

1 Claim, 5 Drawing Sheets

|  | 0th COLUMN | 1st COLUMN |  | — — — — — — — — | 15th COLUMN |
|---|---|---|---|---|---|
| Y | DIM(15,0) | DIM(15,1) | DIM(15,2) | — — — — — — — — | DIM(15,15) |
|  | ⋮ | ⋮ | ⋮ |  | ⋮ |
|  | DIM(2,0) | DIM(2,1) | DIM(2,2) | — — — — — — — | DIM(2,15) |
|  | DIM(1,0) | DIM(1,1) | DIM(1,2) | — — — — — — — | DIM(1,15) |
|  | DIM(0,0) | DIM(0,1) | DIM(0,2) | — — — — — — — | DIM(0,15) |

X

SCATTER VS. RED-FL DISTRIBUTION WITH ROTATION

METHOD OF DEMARCATING TWO-DIMENSIONAL DISTRIBUTION

BACKGROUND OF THE INVENTION

This invention relates to a method of demarcating a two-dimensional distribution in which, when a specimen containing two or more types of particle groups is measured by a particle analyzer capable of measuring two analytical parameters regarding various particles of interest, one particle group is differentiated from other particle groups by drawing a discriminant on a plot of a two-dimensional distribution in which the two analytical parameters are adopted as the two axes.

In order to demarcate one particle group from another particle group in particle analysis, a common practice in the art is to draw a plot of a two-dimensional distribution regarding the particles of interest and draw a discriminant within the plot of the distribution. For example, the specification of U.S. Pat. No. 4,325,706 describes a method of measuring a blood sample, which is fluorescently dyed with acridene orange, by means of a flow cytometer, and differentiating the particle groups in the blood sample by drawing a discriminant within a plot of a two-dimensional distribution prepared from signals indicative of fluorescence and scattering detected from individual particles. FIG. 9 is a view of FIG. 8B of the drawings in the above-mentioned specification. The horizontal axis represents the signal strength of red fluorescence detected from the particles, and the vertical axis represents the signal strength of scattered light detected from the particles. A red blood cell (RBC) particle group and a reticulocyte (RETICS) particle group in the center of the view are demarcated from a platelet (PLT) particle group by a diagonally extending linear discriminant.

In a case where particle groups on a plot of a two-dimensional distribution are differentiated by a linear discriminant as set forth above, the manner in which the discriminant is drawn is simple and no particular problems are encountered. In actual practice, however, there are many instances in which it is necessary to draw a more complicated discriminant. Since the acridine orange used in the aforesaid U.S. patent exhibits strong background fluorescence due to the dye solution itself, the dye tends to produce an error in the measurement of the intensity of fluorescence ascribable to the blood cells. Thus, it has been found that this dye is difficult to actually use. These findings are set forth in the specification of Japanese Patent Application Laid-Open (KOKAI) No. 61-280565. Accordingly, the same publication discloses use of a more practical dye (auramine 0) instead of acridine orange as a reagent for measuring reticulocytes. When auromine 0 is used, however, the red blood cell particle group and reticulocyte particle group cannot be demarcated from the platelet particle group by a simple linear discriminant, as shown in FIG. 1. Here the horizontal axis represents the relative intensity of fluorescence and the vertical axis the relative intensity of forward-scattered light. Each point in FIG. 1 corresponds to an individual particle, A represents the red cell particle group, B the reticulocyte particle group and C the platelet particle group. The curved line in FIG. 1 is a discriminant which demarcates the red cell particle group and reticulocyte particle group from the platelet particle group. The vertically extending straight line in the plot of FIG. 1 does not have a direct bearing upon the present invention but is a discriminant distinguishing the red blood cell group from the reticulocyte particle group. This line is shown for reference purposes only.

The characters and lines in FIGS. 2 through 6 have the same meansings. FIG. 1 is a plot of results obtained when measuring the blood sample of a healthy individual. When a specimen having an idiosyncrasy is measured, however, the distribution of the platelet particle group (C) exhibits a greater spread toward the upper right in comparison with the healthy individual, as shown in FIG. 2. As a result, the positions of the discriminants in FIGS. 1 and 2 clearly differ. This means that it is necessary to find an optimum discriminant for each and every sample in order to accurately quantify the number of platelet and/or reticulocyte particles.

SUMMARY OF THE INVENTION

Accordingly, an object of the present invention is to provide a method of demarcating one particle group from other particle groups in a plot of a two-dimensional distribution by introducing a prescribed principle and automatically drawing a discriminant curve for every sample.

According to the present invention, the foregoing object is attained by providing a method of demarcating one particle group in a sample undergoing measurement from other particle groups in the sample by drawing a discriminant in a plot of a two-dimensional distribution, comprising the steps of:

(a) dividing the two-dimensional distribution into a plurality of grid-shaped areas and determining the number of particles contained in each area;

(b) selecting an area containing a minimum number of particles from a plurality of areas forming a specific column;

(c) selecting an area containing a minimum number of particles from areas, which are adjacent the area selected in step (b), from among a plurality of areas forming a column neighboring the specific column;

(d) successively selecting an area containing a minimum number of particles from areas, which are adjacent the area selected in an immediately preceding column, in each column successively adjoining the neighboring column; and (e) setting a representative point in each area selected in each column, obtaining an approximation curve by connecting each of the points, and adopting the approximation curve as a discriminant.

In accordance with the present invention, an optimum discriminant curve of each specimen undergoing measurement can be drawn automatically on a plot of a two-dimensional distribution to accurately demarcate one particle group from another particle group even when demarcation is not possible by a simple linear discriminant. This makes it possible to accurately count the number of particles constituting each particle group.

Other features and advantages of the present invention will be apparent from the following description taken in conjunction with the accompanying drawings.

BRIEF DESCRIPTION OF THE DRAWINGS

FIGS. 1 and 2 are distributions illustrating examples in which discriminants are drawn on plots of two-dimensional distributions by the method of the present invention, wherein FIG. 1 shows the plot of a specimen from a healthy individual and FIG. 2 the plot of a specimen exhibiting an idiosyncrasy;

DESCRIPTION OF THE PREFERRED EMBODIMENT

A preferred embodiment of the method according to the invention will now be described with reference to the drawings.

First, a specific example of an optical system in a flow cytometer used to obtain a two-dimensional distribution in the present embodiment will be described with reference to FIG. 8.

Figure 8:
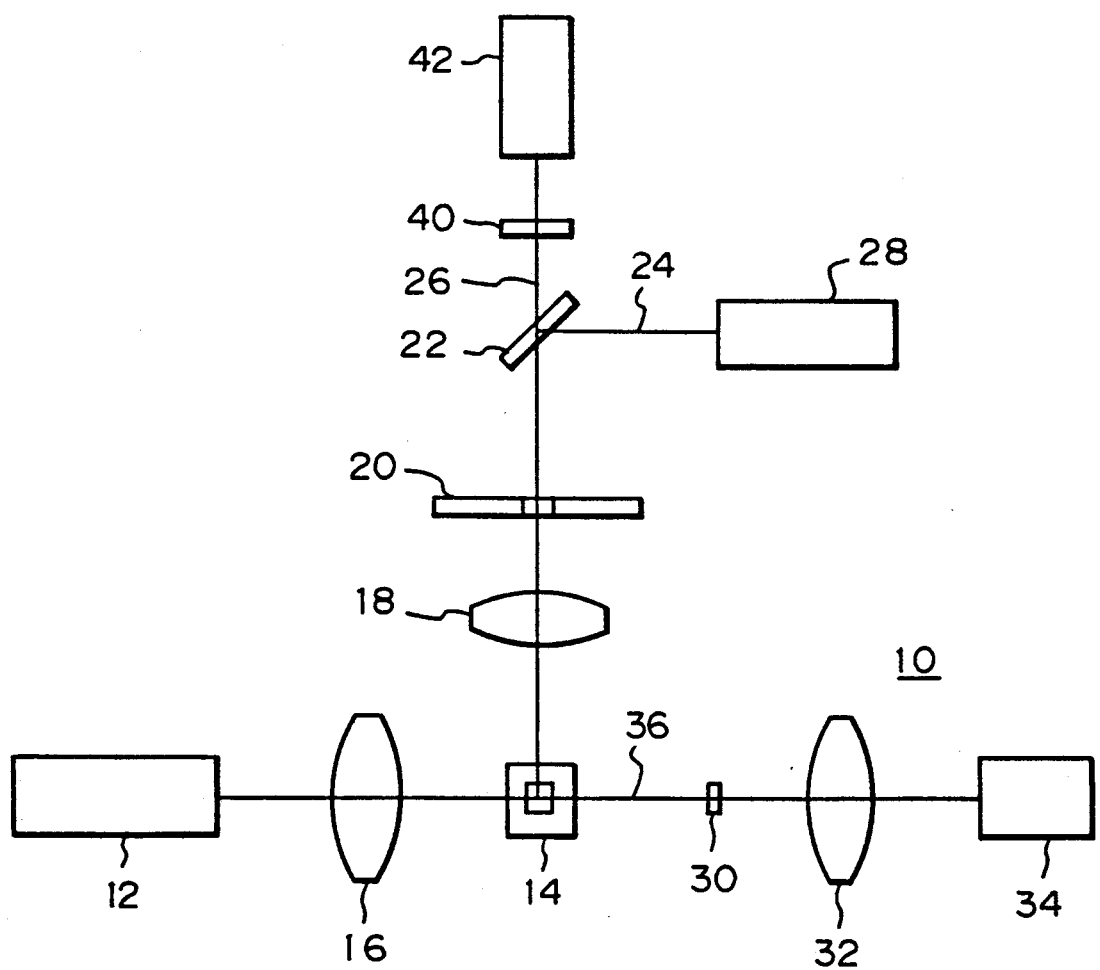
FIG. 8 is a schematic view showing a specific example of the optical system in a flow cytometer used in an embodiment of the present invention.

FIG. 8 illustrates an instance in which forward-scattered light, side-scattered light and fluorescence are measured. The present embodiment deals with a plot of a two-dimensional distribution in which the parameters are the intensity of forward-scattered light and the intensity of fluorescence. However, if the purpose of measurement differs, it is possible to obtain a plot of a two-dimensional distribution using another combination of parameters, such as the strength of side-scattered light and the intensity of fluorescence.

A light source used in an optical system 10 of this flow cytometer is an argon ion laser 12 having a wavelength of 488 nm and an output power of 10 mW. The light emitted by the laser 12 is converged by a cylindrical lens 16 so as to irradiate a specimen flowing through a flow cell 14. When the laser beam impinges upon a particle in the specimen, the beam is scattered. If the particle has been dyed with a fluorescent dye, the irradiated particle emits fluorescence. The side-scattered light and the fluorescence are condensed by a condenser lens 18 and reach a dichroic mirror 22 upon passing through an aperture 20.

The dichroic mirror 22 reflects the side-scattered light, which is shown at numeral 24, and transmits the fluorescence, which is indicated at numeral 26. The side-scattered light reflected by the dichroic mirror 22 is measured by a photoelectron multiplier tube 28. The fluorescence 26 transmitted by the dichroic mirror 22 is measured by a photoelectron multiplier tube 42 upon passing through a color filter 40. The dichroic mirror 22 and photoelectron multiplier tube 28 can be dispensed with if the side-scattered light is not measured.

The laser beam transmitted forwardly through the flow cell 14 and light scattered forwardly along an optic axis 36 by a particle in the specimen are blocked by a beam stopper 30 and therefore do not impinge directly upon a photodiode 34. Light contained in the narrow-angle forward-scattered light that is not blocked by the beam stopper 30 is condensed by the condenser lens 32 and then received by the photodiode 34.

Figure 3:
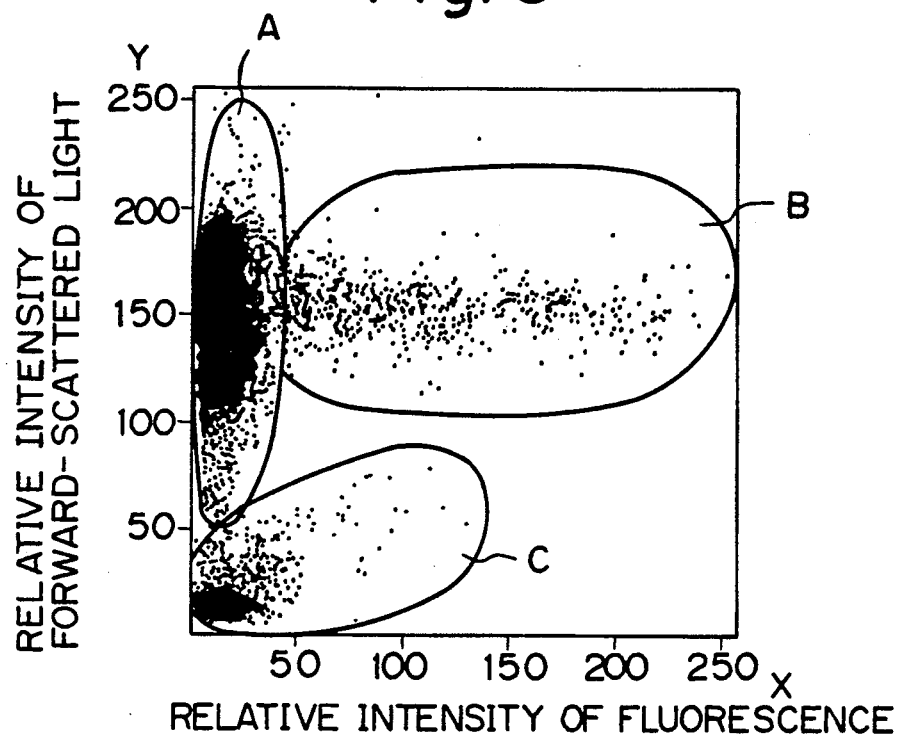
FIG. 3 is a view showing an example of the plot of a two-dimensional distribution obtained when a blood sample is dyed with auramine O and measured by a flow cytometer.

The plot of FIG. 3 is obtained when blood fluorescently dyed with the dye auramine 0 is adopted as the specimen, the specimen is passed through the flow cell 14, fluorescence and side-scattered light are measured by the above-described flow cytometer, and a two-dimensional distribution is plotted with the intensity of fluorescence and the intensity of side-scattered light serving as the two axes. The vertical axis, horizontal axis and characters have the meanings set forth earlier. The intensity of fluorescence and the intensity of side-scattered light are indicated upon being subjected to analog/digital conversion processing in which the full scale is equally divided into 256 resolution graduations. Since reticulocytes are uniquely dyed by auramine 0 and fluorescence when irradiated with laser light, the reticulocyte particle group appears in the enclosed region B. Since the red blood cells exhibit a large scattered light intensity and little fluorescence, the red blood cell particle group appears in the enclosed region A. The platelets exhibit little fluorescent intensity and little scattered light intensity and therefore appear in the enclosed region C. If the number of particles in each of these regions is counted, the number of particles in each particle group present in the specimen can be determined. In order to accomplish this, it is necessary to draw a discriminant on the plot of the two-dimensional distribution for the purpose of demarcating the particle groups. The illustrated embodiment specifically deals with a manner of drawing a discriminant which distinguishes the red blood cell particle group and the reticulocyte particle group (hereinafter an area in which these groups reside shall be referred to as "red blood cell area") from the platelet particle group (hereinafter an area in which this group exists shall be referred to as "platelet area").

Figure 4:
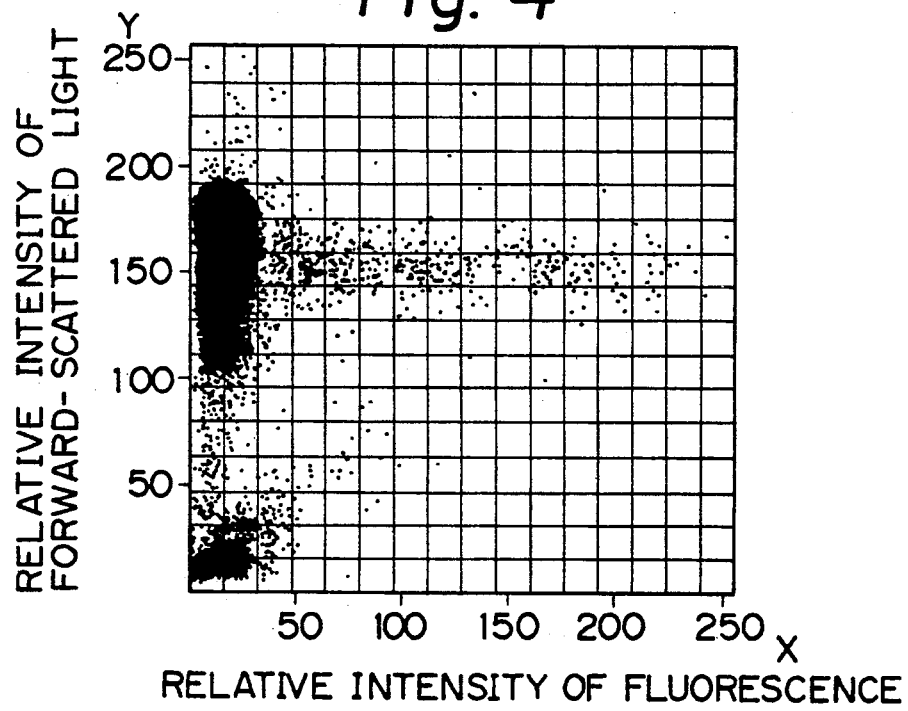
FIG. 4 is a view illustrating the manner in which a two-dimensional distribution is divided into a grid of 16×16 areas.

The distribution of FIG. 3 is divided into 16×16 areas in the form of a grid as shown in FIG. 4. The number of dots (particles) contained in each area is found and the resulting data is substituted into each cell of a two-dimensional 16×16 array corresponding to the 16×16 areas. One example of a two-dimensional array is shown in FIG. 7, in which each cell is denoted by DIM (i,j) (i=0–15, j=0–15).

Figures 7, 9:
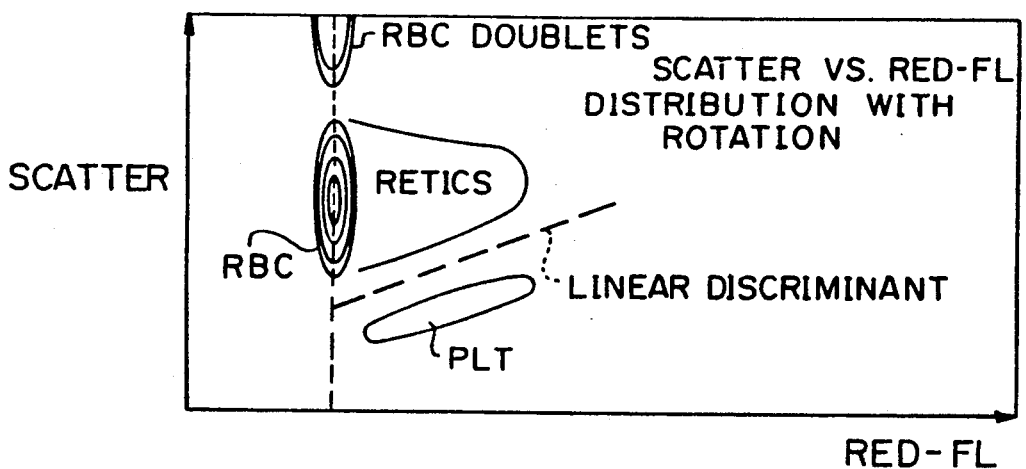
FIG. 7 is a view showing array cells storing the numbers of particles contained in each area.
FIG. 9 is a plot of a two-dimensional distribution showing a discriminant drawn in accordance with the prior-art method.

Each area shown in FIG. 4 corresponds fully to each array cell depicted in FIG. 7, and the horizonal and vertical directions in FIG. 7 correspond to X and Y directions in FIG. 4. Thus, the vertical rows in FIG. 7 shall be referred to as columns.

Next, the boundary between the red cell areas and the platelet areas is found in each column. This is accomplished by successively finding areas (array cells) in which data is sparse in accordance with the following procedure: First, starting with the 0-th column, it is known from experience that the boundary between the red blood cell areas and platelet areas in the 0-th column lies within a range of cells DIM (i,0)(i=0–7) (see FIG. 4). Accordingly, a cell having the smallest value is found from among array cells DIM (i,0) (i=0–7), and the value of i for this cell is substituted in MIN(0). It will be appreciated from FIG. 4 that the areas having a high platelet particle group density reside in the cells of the 0-th column for which i=0 and 1. Therefore, when searching for the above-mentioned areas of sparse particle density, the array cells for which i=0, 1 holds are eliminated in advance and the search can then be restricted to the array cells for which i=2-7 holds. Next, the search proceeds to the 1st column. Since it is expected that the boundary between the red blood cell areas and the platelet areas will be continuous, the range over which the 1st column is searched for areas of sparse data is limited to one near the boundary cell, or DIM[MIN(0), 0], found in the 0-th column. In other words, the cell having the smallest value is retrieved from among the following three cells: DIM[MIN(0)−1,1], DIM[MIN(0), 1], DIM[MIN(0)+1,1], and the i for this cell is substituted into MIN(1). An operation similar to that just described for the 1st column is thenceforth repeated for the 2nd through 15th columns to obtain MIN(2) through MIN(15).

Figure 5:
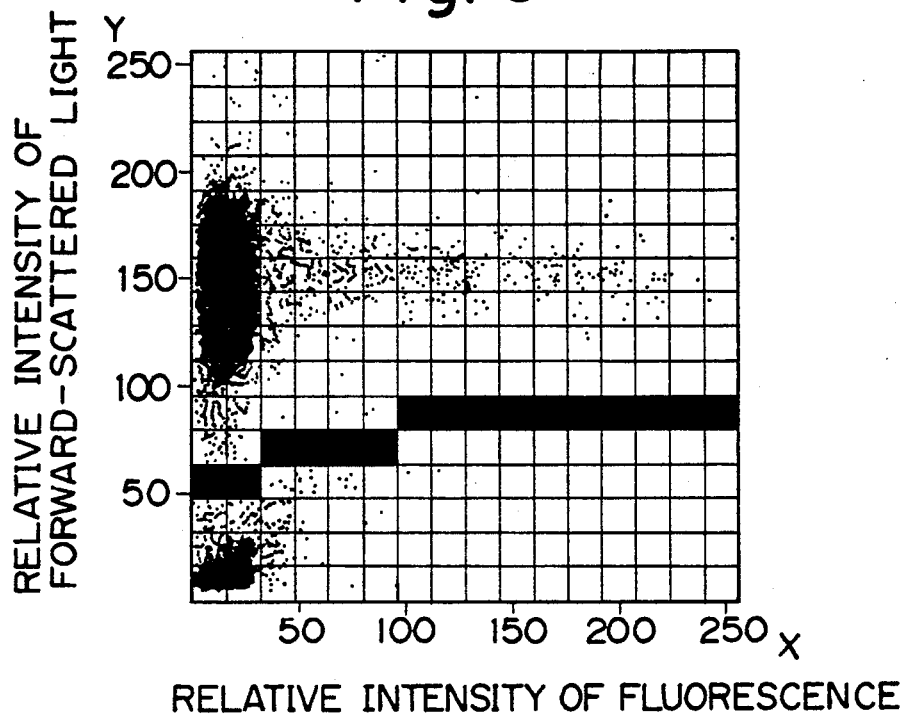
FIG. 5 is a view illustrating the manner in which a series of areas of sparse particle distribution is found in a two-dimensional distribution.

As a result of performing the foregoing operation, areas in the distribution having sparse data are selected. As shown in FIG. 5, these areas are represented by the blackened squares in the grid.

Figure 6:
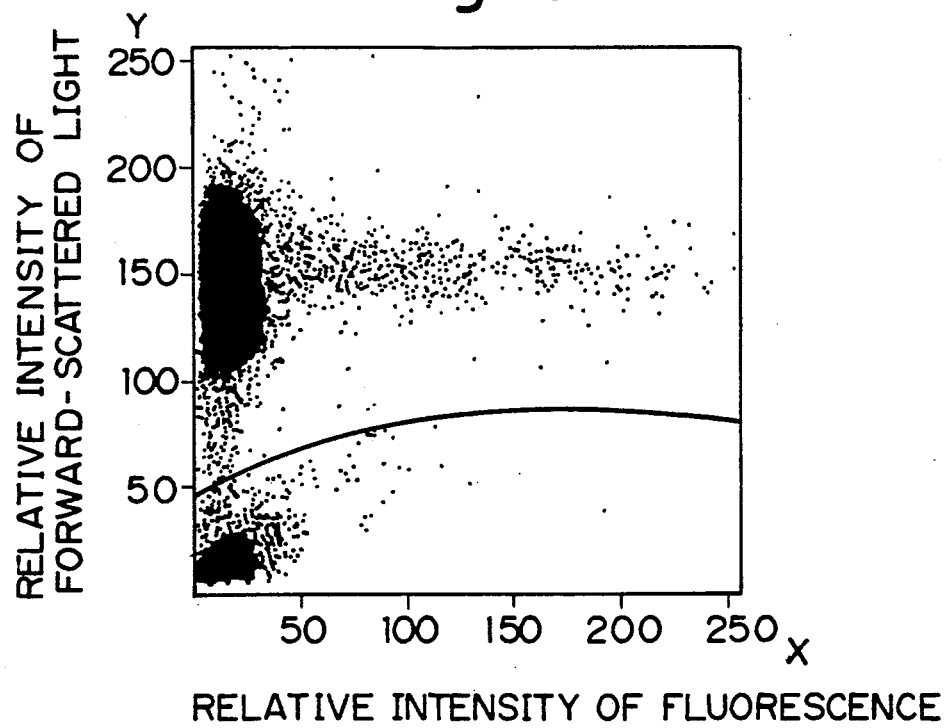
FIG. 6 is a view illustrating a discriminant curve obtained based on the areas of sparse particle distribution shown in FIG. 5.

Next, the coordinate center point of each area represented by a blackened box is adopted as a representative point, and the sixteen representative points are used to obtain a minimum square approximation curve. The curve obtained is as shown in FIG. 6. This is a discriminant which demarcates the red blood cell areas from the platelet areas.

Figure 1:
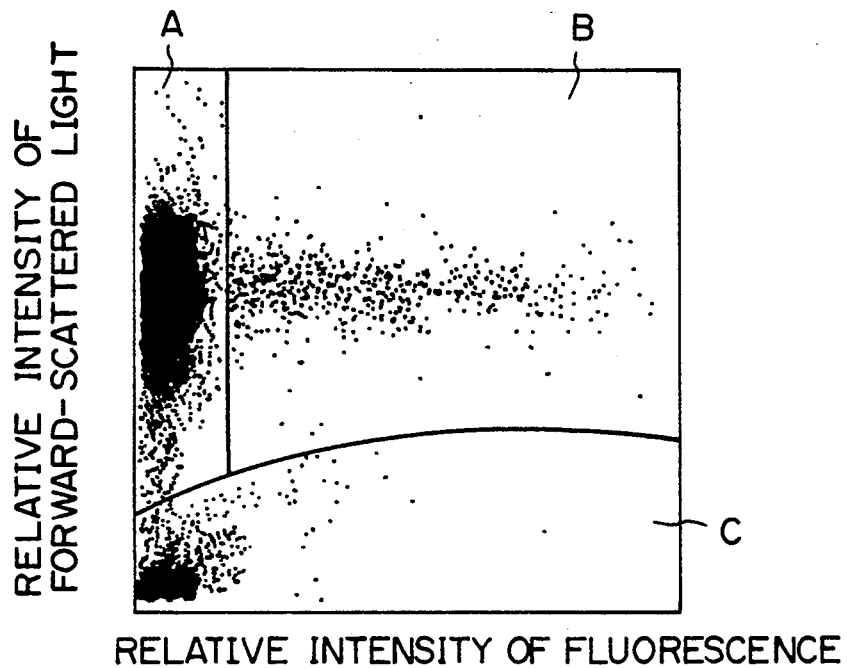
Figure 2:
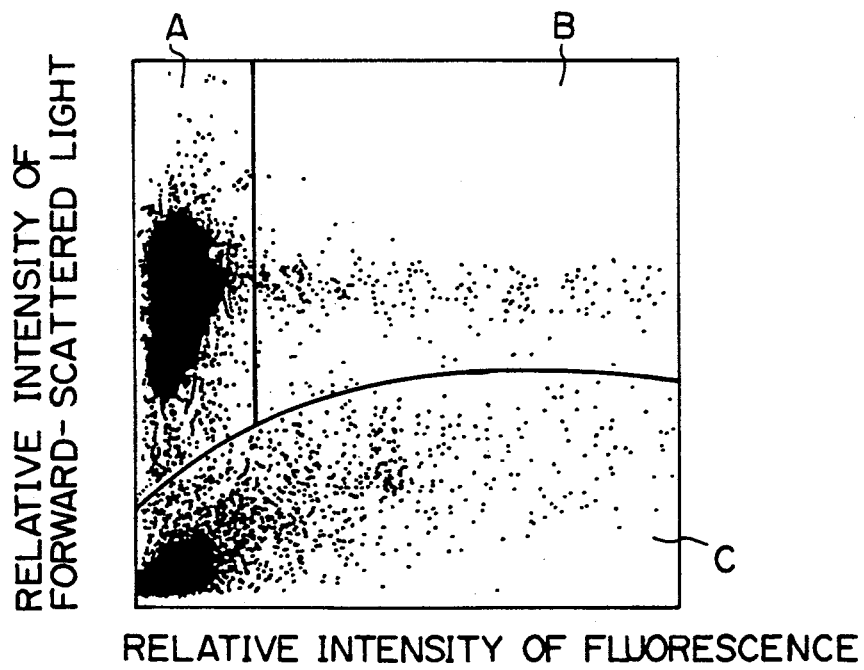

The discriminant curves shown in FIGS. 1 and 2 are also obtained by the above-described method. As shown in both of these figures, the red blood cell areas and the platelet areas are cleanly demarcated. This indicates that the optimum discriminant curve can be obtained for every specimen undergoing measurement.

In the illustrated embodiment, retrieval of areas having sparse data is best performed starting from the leftmost column of FIG. 4, just as described above. However, if there is change in the purpose of measurement, it is possible, depending upon the state of the two-dimensional distribution, to adopt the rightmost column as the 0-th column and begin the retrieval of low-density areas from the rightmost column.

As many apparently widely different embodiments of the present invention can be made without departing from the spirit and scope thereof, it is to be understood that the invention is not limited to the specific embodiments thereof except as defined in the appended claims.

What is claimed is:

1. A method of demarcating in a blood sample having a plurality of blood cell particles, a first particle group consisting of red blood cell particles and reticulocyte particles from a second particle group, said second particle group substantially free of red blood cell particles and reticulocyte particles by drawing a discriminant in a plot of a two-dimensional distribution prepared from signals indicative of fluorescence and scattered light detected from individual particles, comprising the steps of:

(a) preparing a specimen for measuring by mixing a sample of blood with a fluorescent dye solution, said dye solution comprising a fluorescent dye which is capable of dyeing at least said particles in said first particle group of said blood sample;

(b) introducing an aliquot of the specimen prepared in accordance with step (a), into a flow cell of a flow cytometer, irradiating particles of said aliquot of said specimen in said flow cytometer with a light of a wavelength that excites fluorescence of said fluorescent dye.

(c) measuring from said particles of said aliquot relative intensities of a fluorescence signal due to said fluorescent dye absorbed by said particles and relative intensities of a signal of scattered light from said wavelength of light;

(d) plotting a two-dimensional distribution on the basis of relative intensities of fluorescence and relative intensities of scattered light.

(e) dividing the two-dimensional distribution into a plurality of grid-shaped areas in the plot and determining the number of particles contained in each area;

(f) selecting an area in the plot containing a minimum number of particles from a plurality of areas forming a specific column;

(g) selecting an area in the plot containing a minimum number of particles from areas, which are adjacent the area selected in said step (f), from among a plurality of areas forming a column neighboring said specific column;

(h) successively selecting an area in the plot containing a minimum number of particles from areas, which are adjacent the area selected in an immediately preceding column, in each column successively adjoining the neighboring column; and (i) setting a representative point in each area in the plot selected in each column, obtaining an approximation curve by connecting each of the points, and adopting the approximation curve as a discriminant.

* * * * *

UNITED STATES PATENT AND TRADEMARK OFFICE
CERTIFICATE OF CORRECTION

PATENT NO. : 5,006,986
DATED : April 9, 1991
INVENTOR(S) : T. Inoue

It is certified that error appears in the above-identified patent and that said Letters Patent is hereby corrected as shown below:

Title Page, item [73] Assignee: change "Toa" to --TOA--.

Column 2, line 5, change "meansings" to --meanings--.

Signed and Sealed this

Twenty-fifth Day of August, 1992

Attest:

DOUGLAS B. COMER

*Attesting Officer*  *Acting Commissioner of Patents and Trademarks*